US006251123B1

(12) United States Patent
Patner

(10) Patent No.: US 6,251,123 B1
(45) Date of Patent: Jun. 26, 2001

(54) THERAPEUTIC DEVICE AND METHOD

(76) Inventor: Michael S. Patner, 105 W. 37th Ave., San Mateo, CA (US) 94403

( * ) Notice: Subject to any disclaimer, the term of this patent is extended or adjusted under 35 U.S.C. 154(b) by 0 days.

(21) Appl. No.: 09/115,808

(22) Filed: Jul. 15, 1998

(51) Int. Cl.[7] .......... A61F 5/00
(52) U.S. Cl. .......... 606/237; 297/411.2; 602/32
(58) Field of Search .......... 482/91, 142; 606/237, 606/240, 130, 238, 242; 297/411.2; 602/32; 128/845, 846, 869, 878, 879

(56) References Cited

U.S. PATENT DOCUMENTS

| | | | |
|---|---|---|---|
| 557,132 | 3/1896 | La Prease . | |
| 635,234 | 10/1899 | Chance . | |
| 826,575 | 7/1906 | Hunter . | |
| 1,029,315 | 6/1912 | Poll . | |
| 1,721,221 | 7/1929 | Jáuregui . | |
| 2,347,859 | 5/1944 | Williams | 155/177 |
| 2,696,868 | 12/1954 | Miller | 155/29 |
| 2,827,110 | 3/1958 | Rising | 155/174 |
| 3,206,249 | 9/1965 | Gateley | 297/416 |
| 3,220,771 | 11/1965 | Doss, Sr. | 297/411 |
| 3,322,460 | 5/1967 | Leverman | 297/156 |
| 3,350,133 | 10/1967 | Schaefer | 297/232 |
| 3,382,000 | 5/1968 | Sully | 297/422 |
| 3,567,283 | 3/1971 | Herbert | 297/410 |
| 4,030,781 | 6/1977 | Howard | 297/397 |
| 4,215,680 | 8/1980 | Okuda | 128/33 |
| 4,456,245 * | 6/1984 | Baldwin | 272/118 |
| 4,607,882 | 8/1986 | Opsvik | 297/195 |
| 4,655,471 | 4/1987 | Peek | 280/242 WC |
| 4,763,952 | 8/1988 | Gaudreau, Jr. | 297/383 |
| 4,890,606 * | 1/1990 | Iams et al. | 602/32 |
| 4,892,352 | 1/1990 | Haywood | 297/195 |
| 5,038,758 * | 8/1991 | Iams et al. | 602/32 |
| 5,405,189 | 4/1995 | Stumpf | 297/353 |
| 5,482,355 | 1/1996 | Franzen, Jr. | 297/410 |
| 5,597,208 | 1/1997 | Bonutti | 297/411.35 |
| 5,690,387 | 11/1997 | Sarti | 297/397 |

* cited by examiner

*Primary Examiner*—Michael A. Brown
*Assistant Examiner*—Benjamin Koo
(74) *Attorney, Agent, or Firm*—Townsend and Townsend and Crew LLP

(57) ABSTRACT

A simple and easy-to-use therapeutic device comprises a pair of spaced arm supports for supporting the arms of the patient. The patient pushes the arms laterally against the arm supports to self-stabilize the shoulder girdle complex and horizontally load the sternoclavicular joints. Controlled movements of the head, neck, shoulder, and/or hip are made effective to create self-participatory healing of various portions of the spinal column by inducing synovial lubrication of the vertebrae. The patient's body can be positioned in different postures for isolating different parts of the spinal column for re-education, including a sitting position on a chair, a kneeling position, and a saddle position on a saddle seat. A head rest prevents or minimizes compensations by the body, and further isolates the movements of the body to promote more effective re-education of specific portions of the spinal column. The device is simple in structure and easy to manufacture. The patient can use the device without assistance, making it ideal for use in the home or office.

19 Claims, 3 Drawing Sheets

THERAPEUTIC DEVICE AND METHOD

BACKGROUND OF THE INVENTION

This invention relates generally to therapeutic devices and methods and, more particularly to a device and a method for enhancing self-participatory structural realignment of the spinal column and promoting the restoration of normal curvature.

The vertebral column's function is to support the trunk and to protect the spinal cord. It lies in the general vertebrate plane, and is median and posterior in the body. Typically, there are 7 cervical (C1–C7), 12 thoracic (T1–T12), 5 lumbar (L1–L5), 5 sacral, and 4 coccygeal vertebrae. The cervical, thoracic, and lumbar vertebrae can be categorized into seven groups with transitional vertebrae defined between adjacent groups: C1–C3, C4–C6, C7–T2, T3–T5, T6–T9, T10–L1, and L2–L5. In a normal vertebral column, there are no curvatures in the coronal plane of the column, but there are well-marked curvatures in the sagittal plane. In adults, the cervical curve extending from the atlas to the second thoracic vertebra (T2) is convex forwards and the least marked, and is called a lordosis. The thoracic curve extending between the second (T2) and the eleventh (T11) and twelfth (T12) thoracic vertebrae is kyphotic (concave forwards). The lumbar curve extending from the twelfth thoracic vertebra (T12) to the lumbosacral angle is lordotic (convex forwards). The pelvic curve is concave anteroinferiorly and involves the sacrum and coccygeal vertebrae, extending from the lumbosacral junction to the apex of the coccyx.

Normal movements between adjacent vertebrae are limited, but the movements have a cumulative effect over the whole column, allowing a considerable degree of bending or rotation. For instance, the upward inclination of the superior articular facets in the cervical region allows free flexion and extension. In the thoracic region, all movements are limited (especially above). Lumbar extension is wider in range than flexion and some lateral flexion and rotation can also occur. The vertebral discs are the principal sites of vertebral column movement. By elastic deformability, they permit tilting and torsion between vertebral bodies, and add compressibility to the column.

Abnormalities of the vertebral column have long afflicted many people. Various abnormalities can be attributed to misalignment of the spinal column, such as scoliosis (abnormal lateral curvature of the spine, frequently accompanied by severe rotation of the vertebral bodies and torsions within the laminae and pedicles), loss of cervical lordosis (abnormal forward curvature of the cervical spine), nerve impingement, and degenerate intervertebral discs disposed between adjacent surfaces of vertebral bodies from the C2 vertebra (axis) to the sacrum. Misalignment is a term used herein to represent loss of normal curvature as well as abnormal lateral curvature in the vertebral column. These abnormalities typically lead to progressive decline in vertebral column mobility. In sum, spinal column misalignment can cause immense pain and severe loss of mobility of the head, neck, back, and other parts of the human body associated with the column.

One way of regaining the partial or full mobility in the body is to attempt to realign the spinal column by reeducating the body gradually via self-participatory exercises. U.S. Pat. No. 3,567,283 issued to Herbert on Mar. 2, 1971 discloses an apparatus for cervico-dorsal re-education in a sitting position. The apparatus is a chair having a back which is perpendicular to a bottom, and a head-holder. The chair back is equipped with a mobile, alternate side quadrilateral travel device sliding in a plane perpendicular to the back. The patient is strapped to the chair with the shoulders held against the chair back. The patients reportedly executes a thrust on the head-holder in a so-called double chin cervical static by contracting the cervico-dorsal muscles. The thrust allows the sliding quadrilateral device to travel horizontally against a resisting weight to create a so-called double-acting dynamic effect to re-educate the cervico-dorsal. The apparatus is complicated and is not easy to use, and is limited to cervico-dorsal re-education.

Despite the advances in medical science, effective and simple method and apparatus of re-educating the body to regain mobility in the vertebral column is lacking.

SUMMARY OF THE INVENTION

The present invention provides therapeutic device and method that avoid the problems and disadvantages of the prior art. This goal is accomplished by providing a therapeutic device that is simple in structure, easy to use, and effective in re-educating the body to realign the spinal column and regain mobility thereof. Realignment is used herein to represent the recovery of normal curvature of the vertebral column.

To promote the effective realignment of the spinal column through self-participatory exercises, it is important to stabilize a portion of the column and isolate the other portions of the column for re-education. The inventor has discovered that a patient can self-stabilize the shoulder girdle complex by pushing the arms outwardly against arm supports. Controlled lateral movement of the head, neck, shoulder, and/or hip are made effective to create healing of the spinal column by inducing synovial lubrication of the vertebrae. The patient's body can be positioned in different postures for isolating different parts of the spinal column for re-education.

In accordance with an aspect of the invention, a therapeutic device comprises a pair of spaced arm supports for supporting a pair of arms of a body. Each arm support has a support portion for supporting a weight of the arm and an outer portion coupled to the support portion and disposed outwardly thereto relative to the body. The outer portions are spaced from each other by substantially a width of a shoulder of the body.

In accordance with another aspect of the invention, a therapeutic device comprises means disposed on two sides of a body for countering lateral forces pushing a pair of arms of the body outwardly from the body away from each other, and maintaining the arms in a substantially fixed lateral relationship with each other with respect to the body. The device includes a head support for supporting a head of the body substantially against forward or backward movements of the head relative to the arms.

Another aspect of the invention is a therapeutic device comprising means for supporting a weight of a pair of arms of a body in a spaced relationship with each other at substantially the same level relative to a shoulder of the body. A pair of spaced supports are provided for resisting lateral movement of the pair of arms pushing outwardly from the body to substantially stabilize a portion of a spinal column of the body.

Yet another aspect of the invention is a therapeutic chair comprising a seat. A pair of spaced arm rests are disposed on two sides of the seat and have lateral arm constraints. A head rest is disposed above the seat and behind the spaced arm rests.

In accordance with still another aspect of the invention, a method for treating a spinal column of a body comprises the step of supporting a weight of a pair of arms of a body. Lateral movement of the pair of arms pushing outwardly from the body is resisted to substantially stabilize a portion of the spinal column including the shoulder girdle complex. The body is supported for movement of another portion of the spinal column relative to the stabilized portion of the spinal column.

BRIEF DESCRIPTION OF THE DRAWINGS

The specific embodiments of this invention, illustrating all their features, will now be discussed in detail. These embodiments depict the novel and nonobvious therapeutic device of this invention shown in the accompanying drawings, which are included for illustrative purposes only. These drawings include the following figures, with like numerals indicating like parts.

DESCRIPTION OF THE SPECIFIC EMBODIMENT

This invention recognizes the importance of stabilizing the body and isolating the afflicted portion of the spinal column to promote effective re-education and realignment of the afflicted portion. Specifically, stabilizing the shoulder girdle complex of the body allows gentle exercises of the head, neck, shoulder, and/or hip to create healing of the spinal column. The shoulder girdle complex includes three vertebrae (C7, T1, and T2), two scapulas (the two flat triangular bones forming the back part of the shoulder), the sternum, and first and second ribs. The group of vertebrae C7–T2 acts as a dynamic unit, and is selected for stabilization because the T1 vertebra interfaces with the sternoclavicular joints in the front and with the first rib which attaches to the back of the body. After the shoulder girdle complex is stabilized, specific, controlled movements of the body parts associated with the afflicted portion of the spinal column are used to gradually realign the spinal column and regain mobility.

In the present invention, the shoulder girdle complex is a base that is stabilized by providing a resistance against lateral movement of the arms of the body pushing outwardly from the body. This horizontally loads the sternoclavicular joints in the front of the base, as they are designed to be loaded. The sternoclavicular joints afford a great deal of movement and has the capacity for repairing the spinal column. Fine tuning of the spinal column alignment occurs at the sternoclavicular joints. The horizontal loading puts the sternoclavicular joints in a position of equilibrium with respect to the weight of the head and neck, providing optimal conditions for re-education. Involved in the sternoclavicular joints are the sternal end of the clavicle and the sternal clavicular notch, together with the adjacent superior surface of the first costal cartilage. The shoulder girdle complex is a base that, when stabilized, facilitates controlled lateral movements and the rotation of specific portions of the vertebral column. These movements cause the synovial fluid to lubricate the joints of the vertebrae to gradually restore mobility. The synovial fluid provides nutrition of articular cartilages, discs, and menisci for joint surfaces, and lubrication and reduction of erosion. Examples of controlled movements of specific portions of the vertebral column are discussed below.

Specific Embodiments of the Therapeutic Device

Figure 1A:
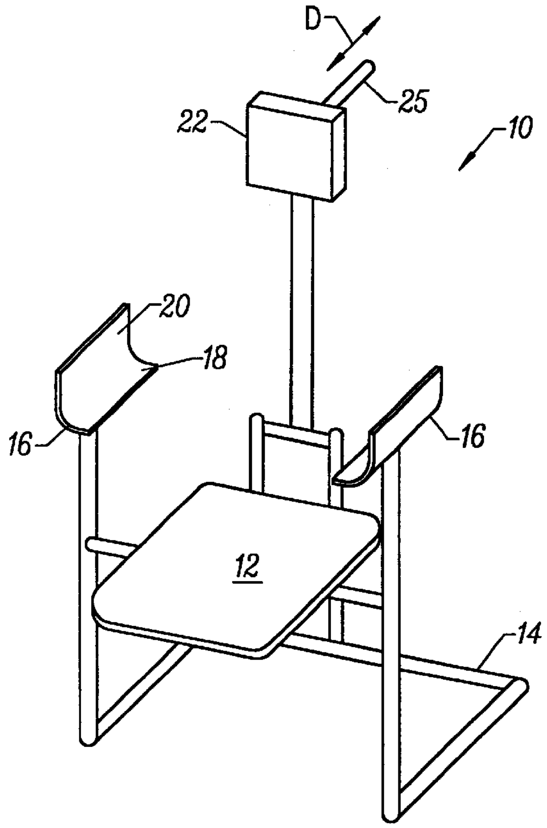
FIG. 1*a* is a perspective view illustrating a therapeutic device for a sitting position in accordance with an embodiment of the present invention.
Figure 1B:
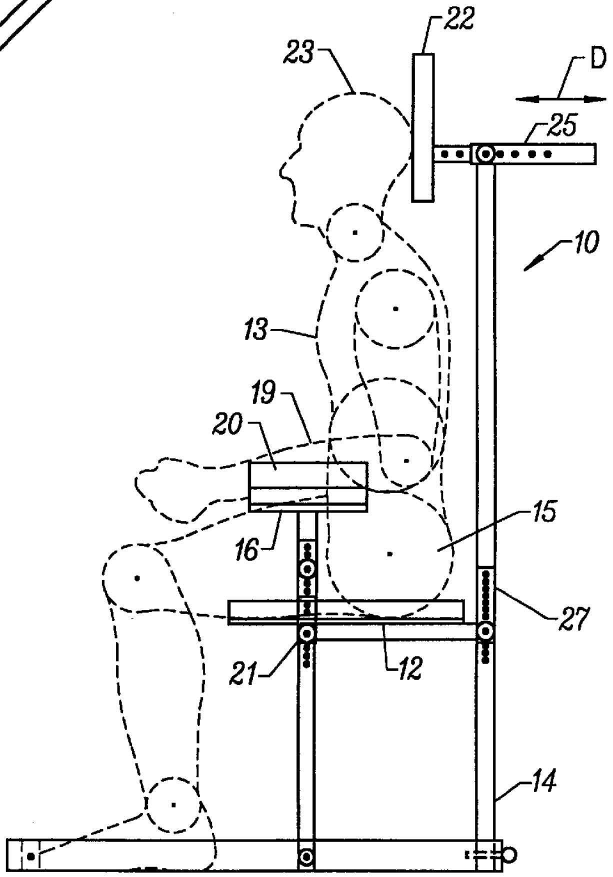
FIG. 1*b* is a side elevational view of the therapeutic device of FIG. 1*a;*

FIGS. 1*a* and 1*b* show a first embodiment of the therapeutic device in the form of a therapeutic chair 10 for treating a patient in a sitting position. The chair 10 includes a seat 12 supported by a support structure 14 on the floor. The seat 12 supports the buttocks 15 of a body 13 sitting on the chair 10, as best seen in FIG. 1*b*. The seat 12 typically is substantially flat and padded. The chair 10 may also include a back support (not shown).

The chair 10 has a pair of arm rests or supports 16 which are respectively disposed on the right and left sides of the seat 12. Each arm rest 16 has a support portion 18 for supporting the weight of one of the arms 19 of the body 13 sitting on the chair 10. The support portion 18 is coupled to an outer portion 20 which is disposed outwardly thereto relative to the body 13. The support portions 18 and outer portions 20 typically provide substantially planar contact surfaces for the arms 19 of the body 13, and may be formed of plate-like portions. The support portions 18 are disposed at substantially the same level for supporting the pair of arms 19 on substantially the same level relative to the shoulder of the body 13. The outer portions 20 of the pair of arm rests 16 are spaced from each other by substantially the shoulder width of the body 13, and are typically spaced by slightly more than the shoulder width. The outer portions 20 serve as lateral constraints for resisting lateral movements of the arms 19 pushing outwardly from the body 13 to substantially stabilize the shoulder girdle complex. In specific embodiments, the outer portions 20 are substantially parallel to each other, the support portions 18 are substantially horizontal, and/or the outer portions are substantially vertical. Further, the arm rests 16 may be adjustable in height relative to the seat 12 to accommodate different body heights by a height adjustment mechanism such as the slotted supports 21 shown in FIG. 1*b*.

A head rest or support 22 is desirably provided for supporting the back of the head 23 of the body 13 substantially against forward or backward movements of the head 23 relative to the arm rests 16. The head rest 22 may be substantially planar as shown or contoured to conform to the shape of the head 23. The head rest 22 may be adjustable relative to the seat 12 to accommodate bodies having different heights between the heads and the buttocks. The head rest 22 is preferably adjustable, in a generally forward-backward direction D substantially perpendicular to the lateral plane of the vertebral column of the body 13, for supporting the head 23 at different positions. An example of a suitable adjustment mechanism employs slotted supports 25 as shown in FIG. 1*b*. Another adjustment mechanism employing slotted supports 27 may be used for adjusting the height of the head rest 22, as shown in FIG. 1*b*. Other adjustable mechanisms and can be used for adjusting the head rest 22. The head rest 22 may be substantially fixed or spring loaded (not shown) to support the head 23 by a resistive force.

Figure 2A:
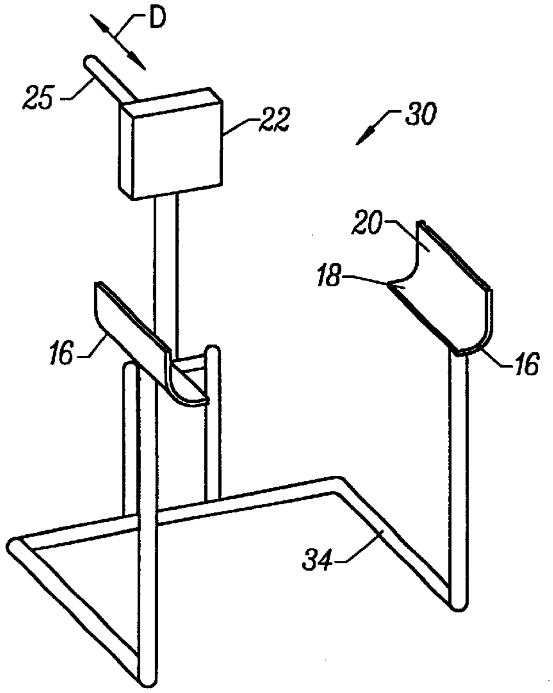
FIG. 2*a* is a perspective view illustrating a therapeutic device for a kneeling position in accordance with another embodiment of the present invention.
Figure 2B:
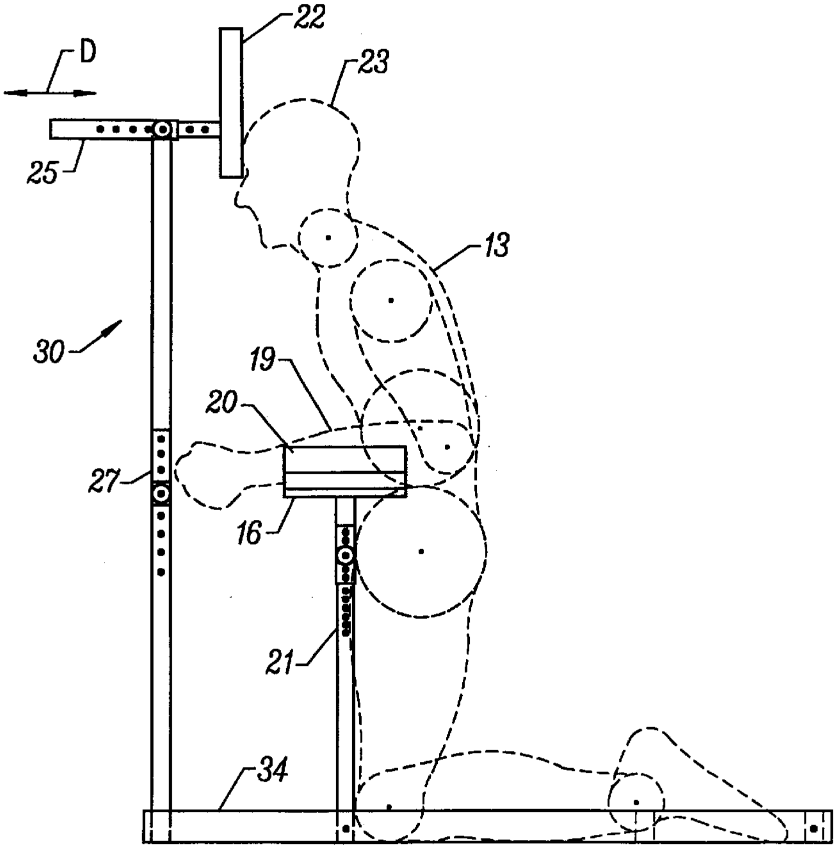
FIG. 2*b* is a side elevational view of the therapeutic device of FIG. 2*a;*

In FIGS. 2*a* and 2*b*, another embodiment of the therapeutic device treats the patient in a kneeling position. To further facilitate an understanding of the present invention, the same reference characters from FIGS. 1*a* and 1*b* are used, where possible, to identify the elements which have the same functions as those described with respect to FIGS. 1*a* and 1*b*. The therapeutic kneeling device 30 includes a pair of arm rests 16 disposed on the right and left sides of the body 13. The arm rests 16 include support portions 18 that are spaced from the floor by a support structure 34 for supporting the pair of arms 19 of the body 13 in the kneeling position. The arm rests 16 may be adjustable in height relative to the floor to accommodate different body heights by a height adjustment mechanism such as the slotted supports 21 shown in FIG. 2*b*. The arm rests 16 may also be adjustable in other direction to accommodate different body sizes (e.g., different shoulder widths and arm lengths). A head rest 22 is desirably provided for supporting the front of the head 23 of the body 13. The head rest 22 is preferably adjustable relative to the arm rests 16 at least in the D direction employing slotted supports 25, and may also employ slotted supports 27 for height adjustment (see FIG. 2*b*).

Figure 3A:
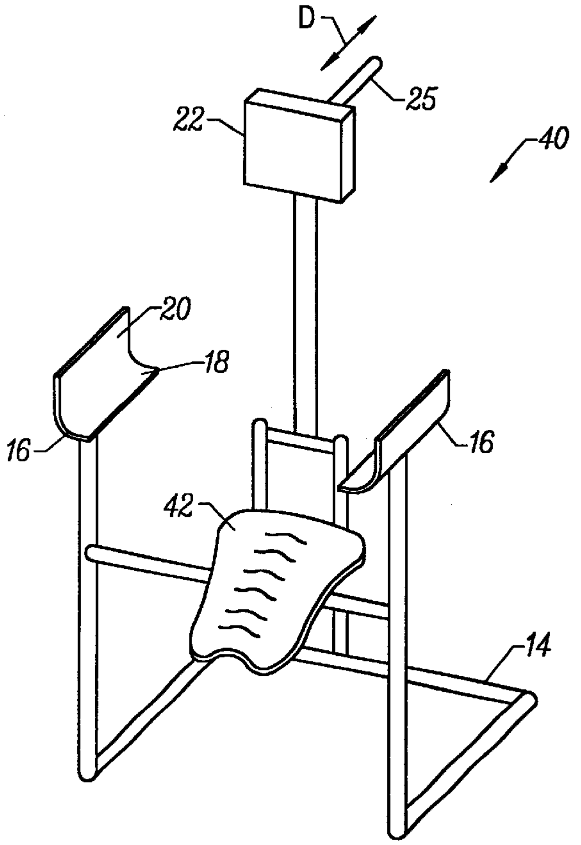
FIG. 3*a* is a perspective view illustrating a therapeutic device in a saddle position in accordance with yet another embodiment of the present invention.
Figure 3B:
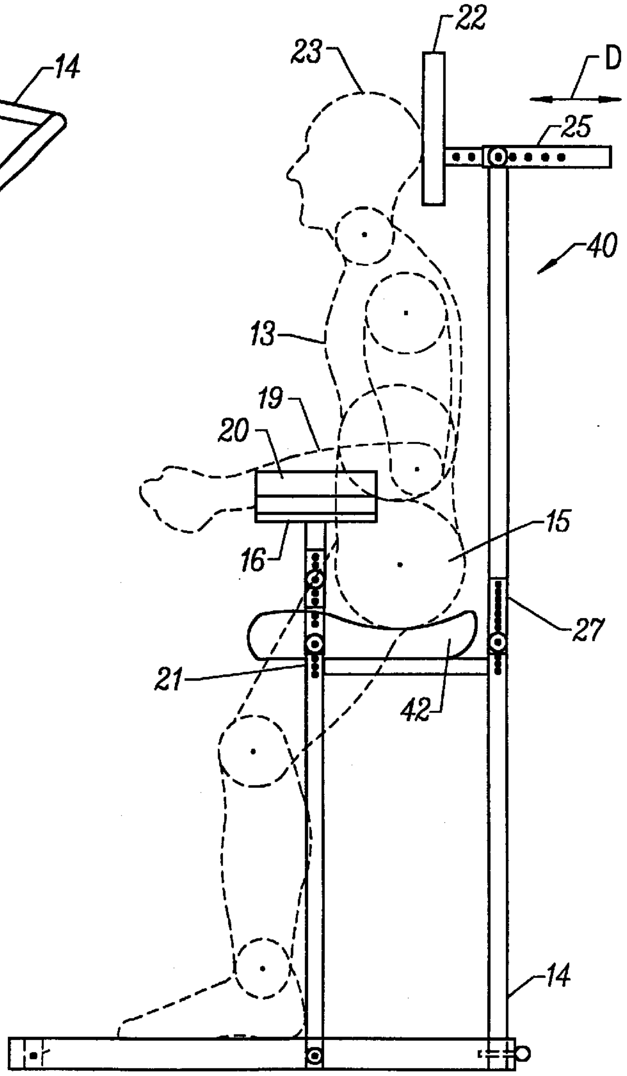
FIG. 3*b* is a side elevational view of the therapeutic device of FIG. 3*a.*

In another embodiment of the therapeutic device shown in FIGS. 3*a* and 3*b*, a therapeutic saddle 40 has a support structure 14 for supporting a pair of arm rests 16 on both sides of the body 13 similar to the therapeutic chair 10 of FIGS. 1*a* and 1*b*. The therapeutic saddle 40 also desirably includes an adjustable head rest 22 that adjustably supports the head 23 at different positions (at least in the D direction). The seat 42 in the therapeutic saddle 40, however, has a saddle-like shape. The saddle seat 42 provides lateral rotational freedom of movement for the buttocks 15 of the body 13. The arm rests 16 may be adjustable in height relative to the saddle 42 to accommodate different body heights by a height adjustment mechanism such as the slotted supports 21 shown in FIG. 3*b*. The head rest 22 is preferably adjustable relative to the arm rests 16 at least in the D direction employing slotted supports 25, and may also employ slotted supports 27 for height adjustment (see FIG. 3*b*).

Operation

When the arms 19 of the body 13 push outwardly and laterally against the outer portions 20 of the arms rests 16, the patient horizontally loads the sternoclavicular joints and stabilizes the shoulder girdle complex. Gentle lateral movements of portions of the spinal column create healing of the column. The C1 vertebra of the cervical spine does not lose mobility unless the neck is broken. Therefore, recovery of mobility typically starts from the C1 vertebra downward. Repeated, delicate, lateral movements of the spinal column allow the other vertebrae to gradually adjust to the movement of the C1 vertebra as the synovial fluid lubricates the joints of the vertebrae and to gradually restore mobility. The different embodiments of the therapeutic device (10, 30, 40) are designed to isolate and optimize conditions for different portions of the spinal column for controlled exercise and re-education.

When the body 13 sits on the therapeutic chair 10 of FIGS. 1 and 2 with the arms 19 resting on the arm rests 16, the head 23 is centered and balanced relative to the shoulder to provide optimal conditions for re-education. By pushing the arms 19 outwardly against the outer portions 20 of the arm rests 16, the cervical vertebrae (C1–C7) are isolated for reeducation by side-to-side lateral movements of the head 23. The cranium or skull moves laterally relative to the C1 vertebra and the motion is transferred downward. Healing occurs gradually from the C1 vertebra down toward the C7 vertebra, substantially restoring lateral flexibility of the neck and range of mobility of the head and neck. The body 13 may be inclined to compensate itself in response to the movements of the head 23. Supporting the head 23 with the head rest 22 prevents or minimizes compensations by the body 13, and further isolates the movements of the head 23. The head rest 22 holds the cranium in place and allows specific movements to occur at the joint segment between the cranium and the C1 vertebra to exercise the cervical spine from the C1 vertebra downward for more effective healing. The exercise stimulates muscle activity that gradually realigns the cervical spine and allows the head 23 to straighten out. The body 13 is typically sitting in an upright position, although slight incline forward or backward is possible.

After substantial mobility is regained in the cervical vertebrae, the patient can extend the healing down the entire spinal column including the thoracic, and lumbar vertebrae. This exercise employs the kneeling device 30 of FIGS. 2*a* and 2*b*. In the kneeling position, the weight of the upper body is balanced on the knees and the spinal column is centered over the pelvis to provide optimal conditions for re-education. When the body 13 pushes the arms 19 outwardly against the outer portions 20 of the arm rests 16, the spinal column is positioned for re-education by side-to-side lateral movements of the head, neck, and shoulder. The body 13 is desirably leaned forward with the arms 19 pushed against the outer portions 20. Healing occurs in the spinal column gradually from the C1 vertebra downward, restoring mobility of the head, neck, shoulder, and back. Supporting the head 23 with the head rest 22 prevents or minimizes compensations by the body 13, and further isolates the movements of the head 23 to exercise the cervical, thoracic, and lumbar vertebrae from the T1 vertebra downward for more effective healing.

The therapeutic saddle 40 of FIGS. 3*a* and 3*b* allows the body 13 to move laterally at the hip joint in addition to the controlled lateral movement of the head, neck, and shoulder. In the sitting position (FIGS. 1*a* and 1*b*), the thighs are at about a 90° angle with respect to the trunk forming a substantial curvature in the column, specifically the lumbar curvature. The saddle seat 42 lessens the curvature and allows the body 13 to sustain a more natural curvature in the lumbar vertebrae. This allows the lower back to become a level platform on which the upper body is centered and balanced to provide optimal conditions for re-education. This facilitates controlled exercise of the pelvic girdle, which includes the pubic, ilium, and ischium bones, the hip joint, and the sacrum. The pelvic girdle affords a great deal of movement for correction of the lumbar vertebrae to treat lower back problems. When the body 13 pushes the arms 19 outwardly against the arm rests 16, the weight of the body 13 is unloaded at the hip joint. This allows lateral movements of the body 13 at the hip joint (pelvic sliding), which leads to controlled movements of the lumbar vertebrae for creating healing and alignment to treat lower back problems. Supporting the head 23 with the head rest 22 prevents or minimizes compensations by the body 13, and further isolates the movements of the head 23 to exercise the lumber vertebrae from the L1 vertebra downward for more effective healing.

The therapeutic device of the present invention is simple and compact, and easy to manufacture and use. The device can be made at a relatively low cost, and the patient can use the device without assistance, making it ideal for use in the home or office. The device promotes simple and effective self-participatory exercises of the spinal column by allowing the patient to self-stabilize the shoulder girdle complex and isolate portions of the column for re-education. Clinical tests have shown effective treatment of scoliosis. The therapeutic device is widely applicable to correcting different portions of the spinal column.

It will be understood that the above-described arrangements of apparatus and methods therefrom are merely illustrative of applications of the principles of this invention and many other embodiments and modifications may be made without departing from the spirit and scope of the invention as defined in the claims.

What is claimed is:

1. A method for treating a spinal column of a body of a patient, the method comprising:

supporting a weight of a pair of arms of the body;

resisting lateral movement of the pair of arms pushing outwardly from the body of the patient to substantially stabilize a portion of the spinal column including the shoulder girdle complex;

supporting the body for movement of another portion of the spinal column relative to the stabilized portion of the spinal column; and producing lateral movement of a portion of the spinal column relative to the stabilized portion of the spinal column with the pair of arms pushing laterally and outwardly from the body of the patient.

2. The method of claim 1, wherein the step of resisting lateral movement of the pair of arms comprises providing spaced constraints disposed outwardly of the arms.

3. The method of claim 2, further comprising the step of spacing the constraints by substantially a width of a shoulder of the body.

4. The method of claim 2, further comprising the step of spacing the constraints substantially parallel to each other.

5. The method of claim 1, wherein the step of supporting the body comprises supporting buttocks of the body relative to the pair of arms.

6. The method of claim 5, wherein the step of supporting the body comprises substantially immobilizing the buttocks in a sitting position.

7. The method of claim 1, wherein the step of supporting the body comprises supporting the head of the body substantially against forward or backward movements of the head relative to the arms.

8. The method of claim 7 wherein the head of the body is allowed to move laterally.

9. The method of claim 1, wherein resisting lateral movement of the pair of arms pushing outwardly from the body of the patient substantially places the sternoclavicular joints of the patient in a position of equilibrium.

10. The method of claim 9, wherein producing lateral movement of a portion of the spinal column relative to the stabilized portion of the spinal column produces spinal column alignment at the sternoclavicular joints of the patient.

11. The method of claim 1, wherein producing lateral movement of a portion of the spinal column relative to the stabilized portion of the spinal column comprises laterally moving at least one of the head, neck, shoulder, and hip of the patient relative to the stabilized portion of the spinal column.

12. The method of claim 11, wherein at least one of the head, neck, shoulder, and hip of the patient is rotated laterally relative to the stabilized portion of the spinal column.

13. A method for treating a spinal column of a body of a patient, the method comprising:

resting a pair of arms of the body on substantially parallel supports;

pushing the pair of arms laterally and outwardly from the body of the patient against lateral supports to substantially stabilize a portion of the spinal column including the shoulder girdle complex; and producing substantially lateral movement of another portion of the spinal column relative to the stabilized portion of the spinal column with the pair of arms pushed laterally and outwardly from the body of the patient against the lateral supports.

14. The method of claim 13, wherein the pair of arms are spaced by substantially a width of the shoulder of the body on the supports.

15. The method of claim 13, further comprising supporting the buttocks of the body relative to the pair of arms to substantially immobilize the buttocks relative to the stabilized portion of the spinal column.

16. A method for treating a spinal column of a body of a patient, the method comprising:

resting a pair of arms of the body on substantially parallel supports;

pushing the pair of arms laterally and outwardly from the body of the patient against lateral supports to substantially place the sternoclavicular joints of the patient in a position of equilibrium; and producing substantially lateral movement of a portion of the spinal column relative to the sternoclavicular joints with the pair of arms pushed laterally and outwardly from the body of the patient to permit spinal column alignment at the sternoclavicular joints of the patient.

17. The method of claim 16, wherein producing substantially lateral movement of a portion of the spinal column comprises laterally moving at least one of the head, neck, shoulders, and hips of the patient relative to the stemoclavicular joints of the patient.

18. The method of claim 17, wherein at least one of the head, neck, shoulders, and hips of the patient is rotated laterally relative to the sternoclavicular joints of the patient.

19. The method of claim 16, further comprising constraining the head of the body substantially against forward or backward movements of the head relative to the arms.

* * * * *